United States Patent

Cornelissen et al.

Patent Number: 5,962,768
Date of Patent: Oct. 5, 1999

[54] MARKER GENE

[76] Inventors: Marcus Cornelissen, Ellebogten 38, B—9070 Heusden; Arlette Reynaerts, Buisstraat 5, B—9031 Drongen; Véronique Gossele, J. Plateaustraat 7; Roel Van Aarssen, Zwijnaardsesteenweg 35, both of B—9000 Gent, all of Belgium

[21] Appl. No.: 08/549,680

[22] PCT Filed: May 11, 1994

[86] PCT No.: PCT/EP94/01560

§ 371 Date: Jan. 16, 1996

§ 102(e) Date: Jan. 16, 1996

[87] PCT Pub. No.: WO94/26913

PCT Pub. Date: Nov. 24, 1994

[30] Foreign Application Priority Data

May 13, 1993 [GB] United Kingdom ................. 93401237

[51] Int. Cl.⁶ ........................... H01H 5/00; C12N 15/31; C12N 15/54; C12N 15/82; A01H 5/10
[52] U.S. Cl. ........................ 800/300; 800/278; 800/288; 800/294; 800/298; 435/69.1; 435/193; 435/252.2; 435/320.1; 435/418; 435/419; 435/468; 435/469; 536/23.7
[58] Field of Search ................................. 435/320.1, 419, 435/172.3, 69.1, 193, 252.2, 418, 468, 469; 536/23.7; 800/205, 278, 288, 294, 298, 300

[56] References Cited

FOREIGN PATENT DOCUMENTS 0248207  12/1987  European Pat. Off. .
0289478  11/1988  European Pat. Off. .
2601965   1/1988  France .

OTHER PUBLICATIONS

Bevan et al., Nature, 304, 184–187 (1983).
Fraley et al., Proc. Nat. Acad. Sci. USA, 80, 4803–4807 (1983).
Reynaerts et al., Plant Mol. Biology Manual, PMAN–A9 (1987).
Hayford et al., Plant Physiol. 86, 1216–1222 (1988).
Shaw et al., Antimicrobial Agents and Chemotherapy, 33, 2052–2062 (1989).
Carrer et al., Plant Mol. Biology, 17, 301–303 (1991).
Davies, Antibiotics in Laboratory Medicine, 474–489 (ed. V. Lorian).
Phillips et al., British Medical Bulletin, 40, No. 1, 28–35 (1984).
DeBlock et al., The EMBO Journal, 6, No. 9, 2513–2518 (1987).
Nobuta et al., J. Bacteriology, 170, No. 8, 3769–3773 (1988).
Tolmasky, Plasmid, 24, 218–226 (1990).
Van Vhieu et al., J. Bacteriology, 169, No. 12, 5708–5714 (1987).
Davies et al., Ann Rev. Microbiol., 32, 469–518 (1978).
Morohoshi et al., Journal of Antibioties, XXXVII, No. 12, 1687–1691 (1984).
Tenover et al., J. Bacteriology, 170, No. 1, 471–473 (1988).
Ferretti et al., J. Bacteriology, 167, No. 2, 631–638 (1986).
Leemans et al., Gene, 19, 361–364 (1982).

*Primary Examiner*—David T. Fox

[57] ABSTRACT

A method to select and identify transformed plant cells by expressing a chimeric gene encoding an aminoglycoside-6'-N-acetyltransferase in the plant cells in the presence of an aminoglycoside antibiotic.

12 Claims, No Drawings

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 611 base pairs
      (B) TYPE: nucleic acid (C) STRANDEDNESS: single
        (D) TOPOLOGY: linear (ii) MOLECULE TYPE: DNA (synthetic)

(ix) FEATURE:
        (A) NAME/KEY: CDS
        (B) LOCATION: 1..612
        (D) OTHER INFORMATION: /codon_start= 1

(xi) SEQUENCE DESCRIPTION: SEQ ID NO: 1:

```
ATG GAT CCG AGT ATT CAA CAT TTC CAA ACA AAG TTA GGC ATC ACA AAG        48
Met Asp Pro Ser Ile Gln His Phe Gln Thr Lys Leu Gly Ile Thr Lys
 1               5                  10                  15

TAC AGC ATC GTG ACC AAC AGC ACC GAT TCC GTC ACA CTG CGC CTC ATG        96
Tyr Ser Ile Val Thr Asn Ser Thr Asp Ser Val Thr Leu Arg Leu Met
                 20                  25                  30

ACT GAG CAT GAC CTT GCG ATG CTC TAT GAG TGG CTA AAT CGA TCT CAT       144
Thr Glu His Asp Leu Ala Met Leu Tyr Glu Trp Leu Asn Arg Ser His
         35                  40                  45

ATC GTC GAG TGG TGG GGC GGA GAA GAA GCA CGC CCG ACA CTT GCT GAC       192
Ile Val Glu Trp Trp Gly Gly Glu Glu Ala Arg Pro Thr Leu Ala Asp
 50                  55                  60

GTA CAG GAA CAG TAC TTG CCA AGC GTT TTA GCG CAA GAG TCC GTC ACT       240
Val Gln Glu Gln Tyr Leu Pro Ser Val Leu Ala Gln Glu Ser Val Thr
                 70                  75                  80
 65

CCA TAC ATT GCA ATG CTG AAT GGA GAG CCG ATT GGG TAT GCC CAG TCG       288
Pro Tyr Ile Ala Met Leu Asn Gly Glu Pro Ile Gly Tyr Ala Gln Ser
                 85                  90                  95

TAC GTT GCT CTT GGA AGC GGG GAC GGA TGG TGG GAA GAA GAA ACC GAT       336
Tyr Val Ala Leu Gly Ser Gly Asp Gly Trp Trp Glu Glu Glu Thr Asp
                100                 105                 110

CCA GGA GTA CGC GGA ATA GAC CAG TCA CTG GCG AAT GCA TCA CAA CTG       384
Pro Gly Val Arg Gly Ile Asp Gln Ser Leu Ala Asn Ala Ser Gln Leu
        115                 120                 125

GGC AAA GGC TTG GGA ACC AAG CTG GTT CGA GCT CTG GTT GAG TTG CTG       432
Gly Lys Gly Leu Gly Thr Lys Leu Val Arg Ala Leu Val Glu Leu Leu
130                 135                 140

TTC AAT GAT CCC GAG GTC ACC AAG ATC CAA ACG GAC CCG TCG CCG AGC       480
Phe Asn Asp Pro Glu Val Thr Lys Ile Gln Thr Asp Pro Ser Pro Ser
145                 150                 155                 160

AAC TTG CGA GCG ATC CGA TGC TAC GAG AAA GCG GGG TTT GAG AGG CAA       528
Asn Leu Arg Ala Ile Arg Cys Tyr Glu Lys Ala Gly Phe Glu Arg Gln
                165                 170                 175

GGT ACC GTA ACC ACC CCA GAT GGT CCA GCC GTG TAC ATG GTT CAA ACA       576
Gly Thr Val Thr Thr Pro Asp Gly Pro Ala Val Tyr Met Val Gln Thr
                180                 185                 190

CGC CAG GCA TTC GAG CGA ACA CGC AGT GAT GCC TA                       611
Arg Gln Ala Phe Glu Arg Thr Arg Ser Asp Ala
        195                 200
```

(2) INFORMATION FOR SEQ ID NO: 2:

(i) SEQUENCE CHARACTERISTICS:
        (A) LENGTH: 203 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Asp Pro Ser Ile Gln His Phe Gln Thr Lys Leu Gly Ile Thr Lys
 1               5                  10                  15
```

```
Tyr Ser Ile Val Thr Asn Ser Thr Asp Ser Val Thr Leu Arg Leu Met
            20                  25                  30

Thr Glu His Asp Leu Ala Met Leu Tyr Glu Trp Leu Asn Arg Ser His
        35                  40                  45

Ile Val Glu Trp Trp Gly Gly Glu Ala Arg Pro Thr Leu Ala Asp
50                  55                  60

Val Gln Glu Gln Tyr Leu Pro Ser Val Leu Ala Gln Glu Ser Val Thr
65                  70                  75                  80

Pro Tyr Ile Ala Met Leu Asn Gly Glu Pro Ile Gly Tyr Ala Gln Ser
                85                  90                  95

Tyr Val Ala Leu Gly Ser Gly Asp Gly Trp Trp Glu Glu Thr Asp
                100                 105                 110

Pro Gly Val Arg Gly Ile Asp Gln Ser Leu Ala Asn Ala Ser Gln Leu
                115                 120                 125

Gly Lys Gly Leu Gly Thr Lys Leu Val Arg Ala Leu Val Glu Leu Leu
    130                 135                 140

Phe Asn Asp Pro Glu Val Thr Lys Ile Gln Thr Asp Pro Ser Pro Ser
145                 150                 155                 160

Asn Leu Arg Ala Ile Arg Cys Tyr Glu Lys Ala Gly Phe Glu Arg Gln
                165                 170                 175

Gly Thr Val Thr Thr Pro Asp Gly Pro Ala Val Tyr Met Val Gln Thr
            180                 185                 190

Arg Gln Ala Phe Glu Arg Thr Arg Ser Asp Ala
            195                 200
```

(2) INFORMATION FOR SEQ ID NO: 3:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (synthetic)

(ix) FEATURE:
        (A) NAME/KEY: misc_feature
        (B) LOCATION: 1..54
        (D) OTHER INFORMATION: /note= "upstream oligonucleotide
           primer, designated RVA61"

(xi) SEQUENCE DESCRIPTION: SEQ ID NO: 3:

GATGGATCCG AGTATTCAAC ATTTCCAAAC AAAGTTAGGC ATCACAAAGT ACAG    54

(2) INFORMATION FOR SEQ ID NO: 4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (synthetic)

(ix) FEATURE:
        (A) NAME/KEY: misc_feature
        (B) LOCATION: 1..31
        (D) OTHER INFORMATION: /note= "oligonucleotide primer,
           designated OFD15"

(xi) SEQUENCE DESCRIPTION: SEQ ID NO: 4:

AATAATGTCG ACGTCCCCCT CGATGGAAGG G    31

(2) INFORMATION FOR SEQ ID NO: 5:

(i) SEQUENCE CHARACTERISTICS:
    (A) LENGTH: 7811 base pairs
    (B) TYPE: nucleic acid
    (C) STRANDEDNESS: double
    (D) TOPOLOGY: circular (ii) MOLECULE TYPE: DNA (synthetic)

(ix) FEATURE:
    (A) NAME/KEY: misc_recomb
    (B) LOCATION: 1..7811
    (D) OTHER INFORMATION: /label= vector pTRVA3

(ix) FEATURE:
    (A) NAME/KEY: misc_feature
    (B) LOCATION: 194..218
    (D) OTHER INFORMATION: /note= "T-DNA right border"

(ix) FEATURE:
    (A) NAME/KEY: misc_feature
    (B) LOCATION: 484..684
    (D) OTHER INFORMATION: /note= "the 3' end formation and
        polyadenylation region of T-DNA gene 7"

(ix) FEATURE:
    (A) NAME/KEY: CDS
    (B) LOCATION: complement (729..1340)
    (D) OTHER INFORMATION: /note= "the aac(6') coding sequence"

(ix) FEATURE:
    (A) NAME/KEY: promoter
    (B) LOCATION: 1341..1756
    (D) OTHER INFORMATION: /label= 35S promoter (ix) FEATURE:
    (A) NAME/KEY: misc_feature
    (B) LOCATION: 3001..3023
    (D) OTHER INFORMATION: /note= "T-DNA left border sequences"

(xi) SEQUENCE DESCRIPTION: SEQ ID NO: 5:

```
CGAAGCTCGG TCCCGTGGGT GTTCTGTCGT CTCGTTGTAC AACGAAATCC ATTCCCATTC      60

CGCGCTCAAG ATGGCTTCCC CTCGGCAGTT CATCAGGGCT AAATCAATCT AGCCGACTTG     120

TCCGGTGAAA TGGGCTGCAC TCCAACAGAA ACAATCAAAC AAACATACAC AGCGACTTAT     180

TCACACGAGC TCAAATTACA ACGGTATATA TCCTGCCAGT CAGCATCATC ACACCAAAAG     240

TTAGGCCCGA ATAGTTTGAA ATTAGAAAGC TCGCAATTGA GGTCTACAGG CCAAATTCGC     300

TCTTAGCCGT ACAATATTAC TCACCGGTGC GATGCCCCCC ATCGTAGGTG AAGGTGGAAA     360

TTAATGATCC ATCTTGAGAC CACAGGCCCA CAACAGCTAC CAGTTTCCTC AAGGGTCCAC     420

CAAAAACGTA AGCGCTTACG TACATGGTCG ATAAGAAAAG GCAATTTGTA GATGTTAATT     480

CCCATCTTGA AAGAAATATA GTTTAAATAT TTATTGATAA AATAACAAGT CAGGTATTAT     540

AGTCCAAGCA AAAACATAAA TTTATTGATG CAAGTTTAAA TTCAGAAATA TTTCAATAAC     600

TGATTATATC AGCTGGTACA TTGCCGTAGA TGAAAGACTG AGTGCGATAT TATGTGTAAT     660

ACATAAATTG ATGATATAGC TAGCTTAGCT CATCGGGGGA TCTGTCGACG TCCCCCTCGA     720

TGGAAGGGTT AGGCATCACT GCGTGTTCGC TCGAATGCCT GGCGTGTTTG AACCATGTAC     780

ACGGCTGGAC CATCTGGGGT GGTTACGGTA CCTTGCCTCT CAAACCCCGC TTTCTCGTAG     840

CATCGGATCG CTCGCAAGTT GCTCGGCGAC GGGTCCGTTT GGATCTTGGT GACCTCGGGA     900

TCATTGAACA GCAACTCAAC CAGAGCTCGA ACCAGCTTGG TTCCCAAGCC TTTGCCCAGT     960

TGTGATGCAT TCGCCAGTGA CTGGTCTATT CCGCGTACTC CTGGATCGGT TTCTTCTTCC    1020

CACCATCCGT CCCCGCTTCC AAGAGCAACG TACGACTGGG CATACCCAAT CGGCTCTCCA    1080

TTCAGCATTG CAATGTATGG AGTGACGGAC TCTTGCGCTA AACGCTTGG CAAGTACTGT     1140
```

```
TCCTGTACGT CAGCAAGTGT CGGGCGTGCT TCTTCTCCGC CCCACCACTC GACGATATGA    1200

GATCGATTTA GCCACTCATA GAGCATCGCA AGGTCATGCT CAGTCATGAG GCGCAGTGTG    1260

ACGGAATCGG TGCTGTTGGT CACGATGCTG TACTTTGTGA TGCCTAACTT TGTTTGGAAA    1320

TGTTGAATAC TCGGATCCAT CGATTTGTAG AGAGAGACTG GTGATTTCAG CGTGTCCTCT    1380

CCAAATGAAA TGAACTTCCT TATATAGAGG AAGGGTCTTG CGAAGGATAG TGGGATTGTG    1440

CGTCATCCCT TACGTCAGTG GAGATATCAC ATCAATCCAC TTGCTTTGAA GACGTGGTTG    1500

GAACGTCTTC TTTTTCCACG ATGCTCCTCG TGGGTGGGGG TCCATCTTTG GGACCACTGT    1560

CGGCAGAGGC ATCTTGAACG ATAGCCTTTC CTTTATCGCA ATGATGGCAT TTGTAGGTGC    1620

CACCTTCCTT TTCTACTGTC CTTTTGATGA AGTGACAGAT AGCTGGGCAA TGGAATCCGA    1680

GGAGGTTTCC CGATATTACC CTTTGTTGAA AAGTCTCAAT AGCCCTTTGG TCTTCTGAGA    1740

CTGTATCTTT GATATTCTTG GAGTAGACGA GAGTGTCGTG CTCCACCATG TTGACGAAGA    1800

TTTTCTTCTT GTCATTGAGT CGTAAAAGAC TCTGTATGAA CTGTTCGCCA GTCTTCACGG    1860

CGAGTTCTGT TAGATCCTCG ATCTGAATTT TTGACTCCAT GGCCTTTGAT TCAGTAGGAA    1920

CTACTTTCTT AGAGACTCCA ATCTCTATTA CTTGCCTTGG TTTATGAAGC AAGCCTTGAA    1980

TCGTCCATAC TGGAATAGTA CTTCTGATCT TGAGAAATAT ATCTTTCTCT GTGTTCTTGA    2040

TGCAGTTAGT CCTGAATCTT TTGACTGCAT CTTTAACCTT CTTGGGAAGG TATTTGATCT    2100

CCTGGAGATT ATTACTCGGG TAGATCGTCT TGATGAGACC TGCCGCGTAG GCCTCTCTAA    2160

CCATCTGTGG GTCAGCATTC TTTCTGAAAT TGAAGAGGCT AATCTTCTCA TTATCGGTGG    2220

TGAACATGGT ATCGTCACCT TCTCCGTCGA ACTTCTTCC TAGATCGTAG AGATAGAGAA    2280

AGTCGTCCAT GGTGATCTCC GGGGCAAAGG AGATCTTATA ATTAAATGGC CTTCGCTGCC    2340

CATATTATTG GTAACTCAAC AGCATCAATC ACGGGATTTT TCTCGAATTA ATTGCGTCGA    2400

ATCTCAGCAT CGAAATATTC GCCTTTTTCG TCCATTAGAC TATCTATTGT GATGGTGGAT    2460

TTATCACAAA TGGGACCCGC CGCCGACAGA GGTGTGATGT TAGGCCAGGA CTTTGAAAAT    2520

TTGCGCAACT ATCGTATAGT GGCCGACAAA TTGACGCCGA GTTGACAGAC TGCCTAGCAT    2580

TTGAGTGAAT TATGTGAGGT AATGGGCTAC ACTGAATTGG TAGCTCAAAC TGTCAGTATT    2640

TATGTATATG AGTGTATATT TTCGCATAAT CTCAGACCAA TCTGAAGATG AAATGGGTAT    2700

CTGGGAATGG CGAAATCAAG GCATCGATCG TGAAGTTTCT CATCTAAGCC CCCATTTGGA    2760

CGTGAATGTA GACACGTCGA AATAAAGATT TCCGAATTAG AATAATTTGT TTATTGCTTT    2820

CGCCTATAAA TACGACGGAT CGTAATTTGT CGTTTTATCA AAATGTACTT TCATTTTATA    2880

ATAACGCTGC GGACATCTAC ATTTTTGAAT TGAAAAAAAA TTGGTAATTA CTCTTTCTTT    2940

TTCTCCATAT TGACCATCAT ACTCATTGCT GATCCATGTA GATTTCCCGG ACATGAAGCC    3000

ATTTACAATT GAATATATCC TGCCGCCGCT GCCGCTTTGC ACCCGGTGGA GCTTGCATGT    3060

TGGTTTCTAC GCAGAACTGA GCCGGTTAGG CAGATAATTT CCATTGAGAA CTGAGCCATG    3120

TGCACCTTCC CCCCAACACG GTGAGCGACG GGGCAACGGA GTGATCCACA TGGGACTTTT    3180

AAACATCATC CGTCGGATGG CGTTGCGAGA GAAGCAGTCG ATCCGTGAGA TCAGCCGACG    3240

CACCGGGCAG GCGCGCAACA CGATCGCAAA GTATTTGAAC GCAGGTACAA TCGAGCCGAC    3300

GTTCACGGTA CCGGAACGAC CAAGCAAGCT AGCTTAGTAA AGCCCTCGCT AGATTTTAAT    3360

GCGGATGTTG CGATTACTTC GCCAACTATT GCGATAACAA GAAAAAGCCA GCCTTTCATG    3420

ATATATCTCC CAATTTGTGT AGGGCTTATT ATGCACGCTT AAAAATAATA AAAGCAGACT    3480

TGACCTGATA GTTTGGCTGT GAGCAATTAT GTGCTTAGTG CATCTAACGC TTGAGTTAAG    3540
```

```
CCGCGCCGCG AAGCGGCGTC GGCTTGAACG AATTGTTAGA CATTATTTGC CGACTACCTT      3600

GGTGATCTCG CCTTTCACGT AGTGGACAAA TTCTTCCAAC TGATCTGCGC GCGAGGCCAA      3660

GCGATCTTCT TCTTGTCCAA GATAAGCCTG TCTAGCTTCA AGTATGACGG GCTGATACTG      3720

GGCCGGCAGG CGCTCCATTG CCCAGTCGGC AGCGACATCC TTCGGCGCGA TTTTGCCGGT      3780

TACTGCGCTG TACCAAATGC GGGACAACGT AAGCACTACA TTTCGCTCAT CGCCAGCCCA      3840

GTCGGGCGGC GAGTTCCATA GCGTTAAGGT TTCATTTAGC GCCTCAAATA GATCCTGTTC      3900

AGGAACCGGA TCAAAGAGTT CCTCCGCCGC TGGACCTACC AAGGCAACGC TATGTTCTCT      3960

TGCTTTTGTC AGCAAGATAG CCAGATCAAT GTCGATCGTG GCTGGCTCGA AGATACCTGC      4020

AAGAATGTCA TTGCGCTGCC ATTCTCCAAA TTGCAGTTCG CGCTTAGCTG GATAACGCCA      4080

CGGAATGATG TCGTCGTGCA CAACAATGGT GACTTCTACA GCGCGGAGAA TCTCGCTCTC      4140

TCCAGGGGAA GCCGAAGTTT CCAAAAGGTC GTTGATCAAA GCTCGCCGCG TTGTTTCATC      4200

AAGCCTTACG GTCACCGTAA CCAGCAAATC AATATCACTG TGTGGCTTCA GGCCGCCATC      4260

CACTGCGGAG CCGTACAAAT GTACGGCCAG CAACGTCGGT TCGAGATGGC GCTCGATGAC      4320

GCCAACTACC TCTGATAGTT GAGTCGATAC TTCGGCGATC ACCGCTTCCC TCATGATGTT      4380

TAACTTTGTT TTAGGGCGAC TGCCCTGCTG CGTAACATCG TTGCTGCTCC ATAACATCAA      4440

ACATCGACCC ACGGCGTAAC GCGCTTGCTG CTTGGATGCC CGAGGCATAG ACTGTACCCC      4500

AAAAAAACAG TCATAACAAG CCATGAAAAC CGCCACTGCG CCGTTACCAC CGCTGCGTTC      4560

GGTCAAGGTT CTGGACCAGT TGCGTGAGCG CATACGCTAC TTGCATTACA GCTTACGAAC      4620

CGAACAGGCT TATGTCCACT GGGTTCGTGC CTTCATCCGT TTCCACGGTG TGCGTCACCC      4680

GGCAACCTTG GGCAGCAGCG AAGTCGAGGC ATTTCTGTCC TGGCTGGCGA ACGAGCGCAA      4740

GGTTTCGGTC TCCACGCATC GTCAGGCATT GGCGGCCTTG CTGTTCTTCT ACGGCAAGTG      4800

CTGTGCACGG ATCTGCCCTG GCTTCAGGAG ATCGGAAGAC CTCGGCCGTC CGGGCGCTTG      4860

CCGGTGGTGC TGACCCCGGA TGAAGTGGTT CGCATCCTCG GTTTTCTGGA AGGCGAGCAT      4920

CGTTTGTTCG CCCAGCTTCT GTATGGAACG GGCATGCGGA TCAGTGAGGG TTTGCAACTG      4980

CGGGTCAAGG ATCTGGATTT CGATCACGGC ACGATCATCG TGCGGGAGGG CAAGGGCTCC      5040

AAGGATCGGG CCTTGATGTT ACCCGAGAGC TTGGCACCCA GCCTGCGCGA GCAGCTGCCT      5100

CGCGCGTTTC GGTGATGACG GTGAAAACCT CTGACACATG CAGCTCCCGG AGACGGTCAC      5160

AGCTTGTCTG TAAGCGGATG CCGGGAGCAG ACAAGCCCGT CAGGGCGCGT CAGCGGGTGT      5220

TGGCGGGTGT CGGGGCGCAG CCATGACCCA GTCACGTAGC GATAGCGGAG TGTATACTGG      5280

CTTAACTATG CGGCATCAGA GCAGATTGTA CTGAGAGTGC ACCATATGCG GTGTGAAATA      5340

CCGCACAGAT GCGTAAGGAG AAAATACCGC ATCAGGCGCT CTTCCGCTTC CTCGCTCACT      5400

GACTCGCTGC GCTCGGTCGT TCGGCTGCGG CGAGCGGTAT CAGCTCACTC AAAGGCGGTA      5460

ATACGGTTAT CCACAGAATC AGGGGATAAC GCAGGAAAGA ACATGTGAGC AAAAGGCCAG      5520

CAAAAGGCCA GGAACCGTAA AAAGGCCGCG TTGCTGGCGT TTTTCCATAG GCTCCGCCCC      5580

CCTGACGAGC ATCACAAAAA TCGACGCTCA AGTCAGAGGT GGCGAAACCC GACAGGACTA      5640

TAAAGATACC AGGCGTTTCC CCCTGGAAGC TCCCTCGTGC GCTCTCCTGT TCCGACCCTG      5700

CCGCTTACCG GATACCTGTC CGCCTTTCTC CCTTCGGGAA GCGTGGCGCT TTCTCAATGC      5760

TCACGCTGTA GGTATCTCAG TTCGGTGTAG GTCGTTCGCT CCAAGCTGGG CTGTGTGCAC      5820

GAACCCCCCG TTCAGCCCGA CCGCTGCGCC TTATCCGGTA ACTATCGTCT TGAGTCCAAC      5880

CCGGTAAGAC ACGACTTATC GCCACTGGCA GCAGCCACTG GTAACAGGAT TAGCAGAGCG      5940
```

```
AGGTATGTAG GCGGTGCTAC AGAGTTCTTG AAGTGGTGGC CTAACTACGG CTACACTAGA      6000

AGGACAGTAT TTGGTATCTG CGCTCTGCTG AAGCCAGTTA CCTTCGGAAA AAGAGTTGGT      6060

AGCTCTTGAT CCGGCAAACA AACCACCGCT GGTAGCGGTG GTTTTTTTGT TTGCAAGCAG      6120

CAGATTACGC GCAGAAAAAA AGGATCTCAA GAAGATCCTT TGATCTTTTC TACGGGGTCT      6180

GACGCTCAGT GGAACGAAAA CTCACGTTAA GGGATTTTGG TCATGAGATT ATCAAAAAGG      6240

ATCTTCACCT AGATCCTTTT AAATTAAAAA TGAAGTTTTA AATCAATCTA AGTATATAT       6300

GAGTAAACTT GGTCTGACAG TTACCAATGC TTAATCAGTG AGGCACCTAT CTCAGCGATC      6360

TGTCTATTTC GTTCATCCAT AGTTGCCTGA CTCCCCGTCG TGTAGATAAC TACGATACGG      6420

GAGGGCTTAC CATCTGGCCC CAGTGCTGCA ATGATACCGC GAGACCCACG CTCACCGGCT      6480

CCAGATTTAT CAGCAATAAA CCAGCCAGCC GGAAGGGCCG AGCGCAGAAG TGGTCCTGCA      6540

ACTTTATCCG CCTCCATCCA GTCTATTAAT TGTTGCCGGG AAGCTAGAGT AAGTAGTTCG      6600

CCAGTTAATA GTTTGCGCAA CGTTGTTGCC ATTGCTGCAG GCATCGTGGT GTCACGCTCG      6660

TCGTTTGGTA TGGCTTCATT CAGCTCCGGT TCCCAACGAT CAAGGCGAGT TACATGATCC      6720

CCCATGTTGT GCAAAAAAGC GGTTAGCTCC TTCGGTCCTC CGATCGTTGT CAGAAGTAAG      6780

TTGGCCGCAG TGTTATCACT CATGGTTATG GCAGCACTGC ATAATTCTCT TACTGTCATG      6840

CCATCCGTAA GATGCTTTTC TGTGACTGGT GAGTACTCAA CCAAGTCATT CTGAGAATAG      6900

TGTATGCGGC GACCGAGTTG CTCTTGCCCG GCGTCAACAC GGGATAATAC CGCGCCACAT      6960

AGCAGAACTT TAAAAGTGCT CATCATTGGA AAACGTTCTT CGGGGCGAAA ACTCTCAAGG      7020

ATCTTACCGC TGTTGAGATC CAGTTCGATG TAACCCACTC GTGCACCCAA CTGATCTTCA      7080

GCATCTTTTA CTTTCACCAG CGTTTCTGGG TGAGCAAAAA CAGGAAGGCA AAATGCCGCA      7140

AAAAAGGGAA TAAGGGCGAC ACGGAAATGT TGAATACTCA TACTCTTCCT TTTTCAATAT      7200

TATTGAAGCA TTTATCAGGG TTATTGTCTC ATGAGCGGAT ACATATTTGA ATGTATTTAG      7260

AAAAATAAAC AAATAGGGGT TCCGCGCACA TTTCCCCGAA AAGTGCCACC TGACGTCTAA      7320

GAAACCATTA TTATCATGAC ATTAACCTAT AAAAATAGGC GTATCACGAG GCCCTTTCGT      7380

CTTCGAATAA ATACCTGTGA CGGAAGATCA CTTCGCAGAA TAAATAAATC CTGGTGTCCC      7440

TGTTGATACC GGGAAGCCCT GGGCCAACTT TTGGCGAAAA TGAGACGTTG ATCGGCACGT      7500

AAGAGGTTCC AACTTTCACC ATAATGAAAT AAGATCACTA CCGGGCGTAT TTTTTGAGTT      7560

ATCGAGATTT TCAGGAGCTA AGGAAGCTAA AATGGAGAAA AAAATCACTG GATATACCAC      7620

CGTTGATATA TCCCAATGGC ATCGTAAAGA ACATTTTGAG GCATTTCAGT CAGTTGCTCA      7680

ATGTACCTAT AACCAGACCG TTCCTGGATA TTACGGCCTT TTTAAAGACC GTAAAGAAAA      7740

ATAAGCACAA GTTTTATCCG GCCTTTATTC ACATTCTTGC CCGCCTGATG AATGCTCATC      7800

CGGAATTAAT T                                                          7811
```

(2) INFORMATION FOR SEQ ID NO: 6:

(i) SEQUENCE CHARACTERISTICS:
        (A) LENGTH: 203 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asp Pro Ser Ile Gln His Phe Gln Thr Lys Leu Gly Ile Thr Lys
 1               5                  10                  15
```

-continued

```
Tyr Ser Ile Val Thr Asn Ser Thr Asp Ser Val Thr Leu Arg Leu Met
            20                  25                  30

Thr Glu His Asp Leu Ala Met Leu Tyr Glu Trp Leu Asn Arg Ser His
        35                  40                  45

Ile Val Glu Trp Trp Gly Gly Glu Glu Ala Arg Pro Thr Leu Ala Asp
    50                  55                  60

Val Gln Glu Gln Tyr Leu Pro Ser Val Leu Ala Gln Glu Ser Val Thr
65                  70                  75                  80

Pro Tyr Ile Ala Met Leu Asn Gly Glu Pro Ile Gly Tyr Ala Gln Ser
            85                  90                  95

Tyr Val Ala Leu Gly Ser Gly Asp Gly Trp Trp Glu Glu Glu Thr Asp
            100                 105                 110

Pro Gly Val Arg Gly Ile Asp Gln Ser Leu Ala Asn Ala Ser Gln Leu
        115                 120                 125

Gly Lys Gly Leu Gly Thr Lys Leu Val Arg Ala Leu Val Glu Leu Leu
    130                 135                 140

Phe Asn Asp Pro Glu Val Thr Lys Ile Gln Thr Asp Pro Ser Pro Ser
145                 150                 155                 160

Asn Leu Arg Ala Ile Arg Cys Tyr Glu Lys Ala Gly Phe Glu Arg Gln
            165                 170                 175

Gly Thr Val Thr Thr Pro Asp Gly Pro Ala Val Tyr Met Val Gln Thr
            180                 185                 190

Arg Gln Ala Phe Glu Arg Thr Arg Ser Asp Ala
            195                 200
```

MARKER GENE

This invention relates to a chimeric selectable marker gene comprising: a plant-expressible promoter, DNA encoding an aminoglycoside-6'-N-acetyltransferase (the "AAC(6') "), and a 3' end formation and polyadenylation region active in plant cells.

This invention further relates to a process for selecting or identifying transformed plant cells by expressing the chimeric marker gene, encoding the AAC(6'), in the plant cells. The chimeric marker gene confers, on the plant cells, resistance to normally lethal or growth-suppressive concentrations of an antibiotic which is efficiently detoxified by the AAC(6') in the cells.

This invention also relates to a plant cell, stably transformed with the chimeric marker gene, encoding the AAC (6'), and to a plant regenerated from this plant cell.

BACKGROUND OF THE INVENTION

Plant genetic engineering technology has made significant progress during the last decade. It has become possible to introduce stably foreign genes into plants. This has provided exciting opportunities for modern agriculture.

The use of chimeric selectable marker genes in plant cell transformation has considerably simplified the selection of transformed plant cells. For example, by the expression of such a marker gene, transformed plant cells can be made resistant to antibiotics that are cytotoxic or growth-suppressing to non-transformed cells. A commonly used chimeric marker gene contains the neomycin phosphotransferase-II or nptII coding region (Bevan et al (1983) Nature 304, 184–187: Fraley et al (1983) Proc. Natl. Acad. Sci USA 80, 4803–4807). The nptII gene confers resistance to kanamycin, neomycin and G-418 antibiotics on plant cells expressing the gene (Reynaerts et al (1987) Plant Mol. Biol. Manual, Gelvin, S. B. & Schilperoort, R. A. (eds), Kluwer, Dordrecht, sect. A9, pp. 1–16).

Chimeric marker genes have typically contained: a plant-expressible promoter (with a 5' untranslated region); DNA (such as the npt II gene) encoding a selectable marker; and a 3' end formation and polyadenylation region active in plants. Although the versatility of the nptII gene has been confirmed in chimeric marker genes in several plant systems over the years, there have been limitations on its use that have necessitated the development of alternative antibiotic-resistance genes for use in such chimeric selectable marker genes (Hayford et al (1988) Plant Physiol. 86, 1216). Furthermore, in many situations, a second complementary antibiotic-resistance gene has been needed for introduction into plants that have already been transformed with an antibiotic-resistance gene. Such alternative antibiotic-resistance genes already exist, but they often require the use of very toxic substrates and/or they do not allow efficient selection in all plant species. Certainly for species that are routinely vegetatively reproducible, like potato, antibiotic-resistance genes encoding different selectable markers, with different specific substrates, are required when different genes have to be engineered at different times into a plant.

Among the known antibiotic-resistance genes are those encoding aminoglycoside antibiotic-acetylating (AAC) enzymes, four types of which have been characterized (based on the position of the modified amino group of the 2-deoxystreptamine-derived aminoglycosides):AAC(1), AAC(2'), AAC(3) and AAC(6'). See Shaw et al (1989) Antimicrob. Agents & Chemotherapy 33, 2052–2062. High-pressure liquid chromatography (HPLC) analysis has demonstrated the differences among the acetylated products of these four types of enzymes, and aminoglycoside-resistance profiles can be used to identify the presence of each of these types of enzymes in a host strain (Shaw et al (1989) supra).

European patent publication ("EP") 0 289 478 (Rogers et al (1988), Hayford et al (1988) supra, and Carrer et al (1991) Plant Mol. biol. 17, 301–303 describe the selection on gentamycin of plants transformed with an aminoglycoside-3-N-acetyltransferase-encoding gene (the "aac(3) gene"). The aac(3)-IV gene was found to confer resistance to kanamycin (in Petunia), but the level of resistance was, at most, only sufficient for marginal selection (Hayford et al (1988) supra). These publications also describe supertransformation of tobacco, previously transformed with the nptII gene, with the aac(3) gene by selection on gentamycin-containing medium. EP 0 289 478 also describes the use of gentamycin as a substrate in the transformation of petunia, soybean, oilseed rape and alfalfa transformed with the aac(3) gene. Carrer et al (1991) supra also describes the transformation of tobacco plants with an aac(3)-I gene, only conferring resistance to gentamycin, whereby the gentamycin-resistant plants retain their sensitivity to kanamycin. According to Carrer et al (1991) supra, it may be more advantageous to use a selectable marker gene with a narrow substrate specificity in some cases.

The AAC(6')-encoding genes (the "aac(6') genes") constitute a class of different but related genes acetylating the 6' amino group of several aminoglycoside antibiotics. Several bacterial aac(6') genes have been cloned and sequenced. According to Davis (1986) In *Antibiotics in Laboratory Medicine*, pp. 474–489, (ed.) Lorian V., Williams & Wilkins, Baltimore, Md. and Phillips & Shannon (1984) British Med. Bull. 40, 28–35, AAC(6') acetylates tobramycin, kanamycin, amikacyn, neomycin, gentamycin $C_{1A}$ and $C_2$, sissomycin and netilmycin, although with varying efficiencies depending on the kind of AAC(6'). Two subtypes of aac(6') genes have been characterized by their aminoglycoside resistance profiles: aac(6')-I genes and aac-(6') -II genes; the former subclass comprises the aac(6')-IV and -4 genes, and the latter subclass comprises the aac(6')-III gene (Shaw et al (1989) supra). However, other classifications of these genes have also been made.

Another acetyltransferase, phosphinotricin acetyltransferase, has also been found to be capable of conferring a selectable phenotype (i.e., a herbicide resistance) to plant cells (De Block et al (1987) EMBO J. 6, 2513–2518).

EP 0 248 207 (Wohlleben et al, 1987) describes a gentamycin-resistance gene that is active in Streptomyces and is obtainable from a strain of *S. ghanaensis* by total digestion with BglII.

French patent publication 2 601 965 (Courvalin, 1988) describes a bifunctional gene encoding AAC(6') and APH (2") activities, the cloning and sequencing of this gene, and the use of parts of the gene as a DNA probe for detecting antibiotic-resistance developement in bacterial cultures.

SUMMARY OF THE INVENTION

In accordance with this invention is provided a chimeric selectable marker gene (the "chimeric aac(6') gene"), comprising the following operably linked elements in the same genetic locus: a plant-expressible promoter; a DNA sequence encoding an AAC(6') (the "aac(6') DNA"), particularly an aac(6') DNA with the sequence of SEQ ID No. 1, under the control of the promoter; and a 3' end formation and polyadenylation region active in plant cells.

Also in accordance with this invention is provided a method for selecting or identifying transformed plant cells by: transforming the cells with the chimeric aac(6') gene; and then contacting the cells with concentrations of an aminoglycoside antibiotic that are lethal or growth-suppressive to non-transformed plant cells.

Further in accordance with the invention is provided a plant cell, stably transformed with the chimeric aac(6') gene, a plant cell culture and plant regenerated from this plant cell, and a plant transformation vector, a plasmid and an Agrobacterium strain containing the chimeric aac(6') gene.

DETAILED DESCRIPTION OF THE INVENTION

The term "aac(6') DNA" as used herein means a DNA coding sequence encoding a protein (an "AAC(6')") which catalyses the acetylation of the 6' amino group of aminoglycoside antibiotics. This term includes a partly or fully synthetic DNA sequence, as well as a naturally occurring DNA sequence encoding an AAC(6'). Preferred aac(6') DNAs according to this invention include the DNA of SEQ ID No. 1 and substantially similar DNAs, such as the aac(6') DNAs described by Nobuta et al (1988) J. Bacteriol. 170, 3769), Tolmaski (1990) Plasmid 24, 218–226 and Tran van Nhieu and Collatz (1987) J. Bacteriol. 169, 5708. Other aac (6') DNAs of this invention include those described by Davies and Smith (1978) Ann. Rev. Microbiol. 32, 469–518, Morohoshi et al (1984) J. Antibiotics 37, 1687–1691, Tenover et al. (1988) J. Bacteriol. 170, 471, Ferretti et al (1986) J. Bacteriol. 167, 631, and Shaw et al (1989) Antimicrob. Agents and Chemotherapy 33, 2052.

The term "chimeric aac(6') gene" as used herein means a chimeric selectable marker gene comprising the aac(6') DNA, operably linked to a plant-expressible promoter (including a 5' untranslated region) and a 3' end formation and polyadenylation region active in plants. The aac(6') DNA can also be expressed as a fusion protein in a chimeric gene fusion with another transforming DNA, so as to enhance selection for the desired genotype. The construction of this chimeric gene fusion can be carried out according to techniques derived from methods currently used for constructing chimeric genes comprising known markers.

The term "selectable marker gene" as used herein means a DNA sequence, the expression of which in a plant cell confers a selectable phenotype (e.g., antibiotic resistance) to the plant cell.

The term "translationally neutral modifications" as used herein means modifications of a gene or DNA sequence that do not affect the amino acid sequence encoded by the gene or DNA sequence. Preferred examples of such translationally neutral modifications are changes, by means of nucleotide substitutions, of codons into other codons encoding the same amino acids.

The term "suitable substrate" or "suitable substrate antibiotic" as used herein is an aminoglycoside antibiotic (e.g., kanamycin) which is efficiently modified by AAC(6') so that expression of the aac(6') DNA in a plant cell confers resistance on the plant cell to the antibiotic. Hence, the term "substrate of an AAC(6')" as used herein means any aminoglycoside antibiotic which can be modified, i.e. acetylated, by the aac(6') gene product. An aac(6') DNA of this invention can easily be isolated from bacteria by routine procedures after cultivation on a suitable substrate containing normally inhibitory levels of an aminoglycoside antibiotic, such as kanamycin, for example as described by Nobuta et al (1988) J. Bacteriol. 170, 3769. AAC(6') activity can be assayed by conventional methods (Davies (1986) supra; Shaw et al (1989) supra).

Preferably, an aac(6') DNA of this invention is inserted in a plant genome downstream (i.e., 3') of, and under the control of, a promoter which can direct the expression of the gene in plant cells. Preferred promoters include, but are not limited to, the strong constitutive 35S promoter (Odell et al (1985) Nature 313, 810) or duplicated 35S promoter (Kay et al (1987) Science 236, 1299) of cauliflower mosaic virus; 35S promoters have been obtained from different isolates (Hull & Howell (1987) Virology 86, 482–493). Other preferred promoters include the TR1' promoter and the TR2' promoter (Velten et al (1984) EMBO J. 3, 2723). Also preferred are monocot promoters such as the promoters described in EPO 0 342 926 or EP 0 459 643. Alternatively, a promoter can be utilized which is not constitutive but rather is specific for one or more plant tissues or organs. For example, the aac(6') DNA can be selectively expressed in the green tissues of a plant by placing the DNA under the control of a light-inducible promoter such as the promoter of the ribulose-1,5-bisphosphate-carboxylase small subunit gene as described in EP 0 193 259. Another alternative is to use a promoter whose expression is inducible by temperature or chemical factors or a promoter that is expressed preferentially or selectively in the time period or the developmental stage at which cells are selected, such as a callus-specific promoter, which have been used previously with other markers. In any event, it is evident that a promoter for use in this invention must at least allow sufficient expression of the aac(6') DNA in plant cells to confer antibiotic-resistance to the plant cells.

It is preferred that the aac(6') DNA be inserted upstream (i.e., 5') of suitable 3' transcription regulation signals (i.e., transcript 3' end formation and polyadenylation signals). Preferred 3' transcription regulation signals include those of the chalcone synthase gene (Sommer & Saedler (1986) Mol. Gen. Genet. 202, 429), the cauliflower mosaic virus (Mogen et al (1990) The Plant Cell 2, 1261), the octopine synthase gene (Gielen et al (1984) EMBO J. 3, 835) or the T-DNA gene 7 (Velten & Schell (1985) Nucl. Acids Res. 13, 6981).

In accordance with this invention, all or part of an aac(6') DNA of this invention can be stably inserted in a conventional manner into the nuclear genome of a plant cell, and the so-transformed plant cell can be used to produce a transgenic plant showing resistance to aminoglycoside antibiotics. In this regard, a disarmed Ti-plasmid containing the chimeric aac(6') gene in Agrobacterium (e.g., *A. tumefaciens*) can be used to transform a plant cell using the procedures described, for example, in EP 0 116 718 and EP 0 270 822, PCT publication WO 84/02913, EP 0 242 246, De Block (1988) Theor. Appl. Genet. 76 767–774, and Gould et al (1991) Plant Physiol. 95, 426 (which are incorporated herein by reference). Preferred Ti-plasmid vectors contain the chimeric aac(6') gene between the border sequences, or at least located to the left of the right border sequence, of the T-DNA of the Ti-plasmid. Of course, other types of vectors can be used to transform the plant cell, using procedures such as direct gene transfer (as described, for example, in EP 0 233 247), pollen mediated transformation (as described, for example, in EP 0 270 356, PCT publication WO 85/01856, and U.S. Pat. No. 4,684,611, plant RNA virus-mediated transformation (as described, for example, in EP 0 067 553 and U.S. Pat. No. 4,407,956), liposome-mediated transformation (as described, for example, in U.S. Pat. No. 4,536,475) and other methods such as the methods for transforming monocots (e.g., the major cereals including corn, rice, wheat, barley and rye) as described in PCT publication WO 92/09696. In case the plant to be transformed is corn, other recently developed methods can also be used such as, for example, the method described for certain lines of corn by Fromm et al (1990) Bio/Tech. 8, 833, Gordon-Kamm et al (1990) The Plant Cell 2, 603, and Gould et al (1991) supra. In case the plant to be transformed is rice, other recently developed methods can also be used such as, for example, the methods described by Shimamoto et al (1989) Nature 338, 274), Datta et al (1990) Bio/tech. 8, 736 and Hayashimoto et al (1990) Plant Physiol. 93, 857.

In order to improve the expression of the chimeric aac(6') gene of this invention in a plant, the aac(6') DNA can be modified, for example by changing its natural codon usage to form an equivalent artificial aac(6') DNA. Such modifications can include introducing functional introns and/or translationally neutral modifications into the aac(6') DNA sequence in order to eliminate deleterious DNA sequences present in this bacterial DNA, such as are described in PCT patent application PCT/EP92/02547. This can be done directly by modifying (in a translationally neutral manner) such deleterious DNA sequences, inhibiting expression in the plant cells, or indirectly by adapting the codon usage of the aac(6') DNA to that preferred by the plant, for example as described by Murray et al (1989) Nucleic Acids Res. 17, 477. Additionally for achieving sufficient expression in monocot plants such as corn, an efficiently spliced monocot intron, e.g. intron 1 from the corn adh gene, can be added to the chimeric aac(6') gene (Koziel et al (1993) Bio/Tech. 11, 194–200).

A transformed plant of this invention, regenerated from a plant cell transformed with the chimeric aac(6') gene, shows resistance against suitable substrate antibiotics by virtue of the production of AAC(6') activity in its plant cells. Such a plant can be used in a conventional breeding scheme to produce more transformed plants with the same aminoglycoside antibiotic-resistance characteristics or to introduce the chimeric aac(6') gene into other varieties of the same or related plant species by standard breeding techniques. Seeds, which are obtained from the transformed plants, contain the chimeric aac(6') gene as a stable genomic insert.

Since the spectrum of antibiotics which can be chemically modified by expression of an aac(6') DNA of this invention is different from that of the nptII coding region, the aac(6') DNA can be used with the nptII coding region in different chimeric selectable marker genes where two different foreign genes are to be introduced into a plant, with each foreign gene being associated with its own chimeric marker gene. When engineering multiple chimeric marker genes in a plant, it may be advantageous to use a chimeric aac(6') gene only conferring resistance to a limited group of aminoglycoside antibiotics (Carrer et al (1991) supra). However, if only one chimeric marker gene is to be used, it is preferred to use a chimeric aac(6') gene with kanamycin as the suitable substrate for plant cells. In this regard, the enzymatic assay for detecting acetyltransferase activity is often quicker and more convenient to use than the phosphotransferase assay used to detect nptII-activity.

To test for the successful transformation of plants with an aac(6') DNA, different methods are available. For example, antibiotic-resistance can be checked in a callus induction test or a dot application assay; the presence and the activity of AAC (6') can also be analyzed by an enzymatic assay; Western blotting can provide an easy immunological test but is less sensitive; and kanamycin resistance can be followed in the progeny of transgenic plants by the sowing of seeds on kanamycin-containing media.

The following Examples illustrate the invention. Unless otherwise stated in the Examples, all procedures for making and manipulating recombinant DNA are carried out by the standardized procedures described in Sambrook et al, *Molecular Cloning - A laboratory Manual, Second Ed.*, Cold Spring Harbor Laboratory Press, NY (1989) or in Ausubel et al., *Current Protocols in Molecular Biology,* vols. 1 and 2, Current Protocols, USA (1994).

Sequence Listing

SEQ ID No. 1 shows : i) the DNA sequence of an aac(6') DNA which comes from a Shigella plasmid, and ii) the corresponding amino acid sequence encoded by the aac(6') DNA.

SEQ ID No. 2 shows: the amino acid sequence of the AAC(6') protein.

SEQ ID No. 3 shows: the nucleotide sequence of PCR primer "RVA61".

SEQ ID No. 4 shows: the nucleotide sequence of PCR primer "OFD15".

SEQ ID No. 5 shows: the plasmid "pTRVA3" containing a chimeric aac(6') gene with a 35S-2 promoter, the aac(6') DNA of SEQ ID No. 1, and the 3' end formation and polyadenylation region from T-DNA gene 7.

SEQ ID No. 6 shows: the amino acid sequence of the AAC(6') protein.

EXAMPLES

EXAMPLE 1

Cloning of an aac(6')DNA and construction of a chimeric aac(6') gene

The aac(6') DNA was obtained from the mini-Sa plasmid, pGV1106 (Leemans et al (1982) Gene 19, 361–364). The 1.5 Kb PvuII/HindIII fragment of pGV1106, containing the aac(6') DNA, was ligated to the ScaI-linearized plasmid pGSC1600 (Cornelissen & Vandewiele (1989) Nucl. Acids Res. 17, 19–29) after Klenow treatment. The resultant plasmid, pDF1002A, was used as a template for PCR, using the primers RVA61 and OFD15, of SEQ ID Nos. 3 and 4, respectively. RVA61 is complementary to the non-coding strand of the aac(6') DNA and its untranslated sequences in pFD1002A. The SalI/BamHI aac(6') PCR fragment of pFGD1002A was ligated to the 7.2 Kb SalI/BamHI fragment of the plasmid pGSJ290, containing the chimeric gene, P35S-nptII-3'g7, to yield the plasmid, PTRVA3, of SEQ ID No. 5.

pGSJ290 was derived from pGV825 (Deblaere et al (1985) Nucl. Acids Res. 13, 4777–4787), in which a chimeric P35S-nptII-3'g7 gene construct was cloned between T-DNA border repeats. The 3' untranslated end of the T-DNA gene 7 (i.e., 3'g7) was as described by Velten & Schell (1985) aac(6')supra, the nPtII gene was from pKM109/90 (Reiss et al (1984) EMBO J. 3, 3317–3322), and the CaMV 35S promoter (i.e., P35S) was a cauliflower mosaic virus 35S-2 promoter as described in EP 0 193 259 and in Gardner et al (1981) Nucl. Acids Res. 9, 2871–2888. The chimeric p35S-nptII-3'g7 gene construct was cloned between the HpaI and BglII sites of the T-DNA between the right and left border repeats of pGV825.

Due to the introduction of a BamHI restriction site downstream of its translation initiation site, the aac(6') DNA sequence in pTRVA3, as shown in SEQ ID No. 5, contained the amino acids Asp and Pro at amino acid positions 2 and 3, respectively, and contained the chimeric aac(6') gene, P35S-aac(6') -3'g7, including the aac(6') DNA with the sequence of SEQ ID No. 1.

EXAMPLE 2

Selection of aac(6')-transformed tobacco cells on kanamycin

Plasmids pTRVA3 and pGSJ290 were mobilized from *E. coli* into *A. tumefaciens* strain C58C1-Rif® (pGV2260; Deblaere et al (1985) supra) by means of a triparental cross as described by Deblaere et al (1985) supra and EP 0 193 259. The resultant Agrobacteria were selected on minimal A medium (Miller (1972) *Experiments in Molecular Genetics,* Cold Spring Harbor Laboratory Press, Cold Spring Harbor, N.Y.). Tobacco cv Petit Havana SR1 cells were cocultivated with these Agrobacteria, and transformed tobacco cells were selected using antibiotic resistance according to De Block et al (1984) EMBO J. 3, 1681–1689. Agrobacterium strains used for infection of tobacco protoplasts were: C58C1-Rif® (pGV2260) as a negative control, C58C1-Rif® (pGV2260::pTRVA3) which contains the aac(6') DNA, and C58C1-Rif® (pGV2260::pGSJ290) which contains the nptII gene. One week after infection, the protoplasts were transferred to selective media containing one of the following different concentrations of kanamycin sulphate (Km) :0–25–50–100, 200 µg/ml.

Seven weeks after infection, calli started growing from cells cocultivated with C58C1-Rif® (pGV2260::pTRVA3) and C58C1-Rif® (pGV2260::pGSJ290) at all Km concentrations. Protoplasts infected with pGV2260 (negative control) only formed calli on medium without Km. After transfer of the calli to shoot-inducing medium containing 200 µg/ml Km, shoots were readily formed. Southern analysis of DNA extracted from kanamycin-resistant regenerated tobacco plants confirmed the stable integration of the aac(6') DNA.

EXAMPLE 3

Selection of aac(6')-transformed potato cells on kanamycin

Leaf discs of potato variety Yesmina were cocultivated with *Agrobacterium tumefaciens* strains C58C1-Rif® (pGV2260::pTRVA3) and C58C1-Rif® (pGV2260::pGSJ290), carrying the chimeric genes of Example 2 containing either the aac(6') DNA or nptII gene as described by De Block (1988) supra. The leaf discs were transferred to callus induction medium containing 50 µg/ml kanamycin sulphate. About 30% of the leaf discs that were cocultivated with Agrobacterium C58C1-Rif® (pGV2260::pGSJ290) produced growing calli in the presence of kanamycin, while about 70% of the leaf discs that were cocultivated with Agrobacterium C58C1-Rif® (pGV2260::pTRVA3) produced growing calli after culturing for 6 weeks on kanamycin medium. After transfer of the aac(6') -transformed calli to shoot-regenerating medium, shoots readily formed. The regenerated potato plants are found to retain the kanamycin-resistant phenotype. Southern analysis of DNA extracted from the kanamycin-resistant potato plants and their progeny confirms the integration of the aac(6') DNA.

EXAMPLE 4

Assay for enzymatic activity in aac(6')-transformed plants

The tobacco callus and leaf tissue of Example 2 containing the chimeric aac(6') gene, showed AAC(6') activity when tested in a Thin Layer Chromatography (TLC)-acetyltransferase assay for kanamycin. The acetyltransferase assay for determining phosphinotricin-acetyltransferase activity according to De Block et al (1987) EMBO J. 6, 2513–2518 was used, with the exception that kanamycin sulphate was used as a substrate instead of phosphinotricin in a concentration which was twice the concentration of phosphinotricin used by De Block et al (cf. supra), and 2 µl of $^{14}$C-acetylcoenzyme A were added instead of a mixture containing both the radioactive and the non-radioactive form of the enzyme. Upon incubation for 30 minutes at 37° C., the reaction mixture was spotted onto TLC plates, and the reaction products were separated by chromatography in 1-propanol/NH$_4$OH (3/2). Extracts of the calli containing the chimeric aac(6') gene catalyzed the acetylation of kanamycin, while no reaction was observed with extracts of calli from non-transformed SR1 plants and from nptII-expressing calli. Also extracts from leaf tissue of regenerated aac(6')-transformed tobacco plants were found to efficiently acetylate kanamycin.

Needless to say, this invention is not limited to tobacco or potato plants transformed with the aac(6') DNA. It includes any plant, such as tomato, cotton, rapeseed, alfalfa, sunflower, corn, rice, soybean, brassica, sugar beet and other vegetables, transformed with an aac(6') DNA.

Nor is this invention limited to the use of the chimeric aac(6') gene of SEQ ID No. 5 or the aac(6') DNA of SEQ ID No. 1 for transforming plant cells so that they express an AAC(6'). Other natural and artificial chimeric genes and DNA can be used. In this regard, the aac(6') DNA sequences of SEQ ID Nos. 1 and 5 can be modified by: 1) replacing some codons with others that code either for the same or different, preferably the same, amino acids; and/or 2) deleting or adding some codons; provided that such modifications do not substantially alter the properties, especially the capacity to detoxify aminoglycoside antibiotics, of encoded AAC (6').

All publications referred to in this application are hereby incorporated by reference.

What is claimed is:

1. A chimeric selectable marker gene, which when introduced in a plant cell renders said plant cell resistant to kanamycin; said marker gene comprising the following operably-linked DNA regions:
   a) a DNA region comprising a plant-expressible promoter;
   b) a DNA region encoding a polypeptide with the amino acid sequence of SEQ ID NO: 2;
   c) a DNA region comprising suitable 3' transcription regulation signals active in plant cells.

2. The chimeric selectable marker gene of claim 1, wherein said DNA region encoding said polypeptide with the amino acid sequence of SEQ ID NO: 2, comprises the nucleotide sequence of SEQ ID NO: 1.

3. A plant cell transformed with the chimeric selectable marker gene of claim 1 or claim 2, or progeny cells of said transformed plant cell, said progeny cells comprising said chimeric selectable marker gene.

4. A plant comprising the plant cell of claim 3 or progeny plants of said plants, said progeny plants comprising said chimeric selectable marker gene.

5. A seed of the plant of claim 4 comprising said chimeric selectable marker gene.

6. The chimeric selectable marker gene of claim 1 or claim 2, which is integrated in the genome of a plant cell.

7. A plant transformation vector containing the chimeric selectable marker gene of claim 1 or claim 2.

8. The plant transformation vector of claim 7, which comprises a Ti-plasmid.

9. An *Agrobacterium tumefaciens* strain comprising the vector of claim 8.

10. A method for selecting or identifying transformed plant cells using kanamycin, said method comprising the steps of:
    a) transforming plant cells with a foreign DNA comprising the chimeric selectable marker gene claim 1 or claim 2; and
    b) growing said transformed cells in concentrations of kanamycin that are lethal or growth-suppressive to non-transformed cells.

11. A method for rendering a plant cell resistant to kanamycin; said method comprising the step of: transforming the genome of said plant cell with the chimeric selectable marker gene of claim 1 or claim 2.

12. A method for detoxifying kanamycin in a plant cell, the method comprising the step of: introducing the chimeric selectable marker gene of claim 1 or claim 2 in the genome of the plant cell.

* * * * *

UNITED STATES PATENT AND TRADEMARK OFFICE
CERTIFICATE OF CORRECTION

PATENT NO.    : 5,962,768
DATED         : October 5, 1999
INVENTOR(S)   : Cornelissen et al.

It is certified that error appears in the above-identified patent and that said Letters Patent is hereby corrected as shown below:

On the Title page, please insert item "[73] Assignee:" as follow:
--[73] Assignee: Plant Genetic Systems N.V., Brussels, Belgiun--

On the Title page,
Line 19, under "Other Publications", please change "Van Vhieu et al." to --Van Nhieu et al.

Column 6:
Line 53, change "nPtll" to --nptll--.

UNITED STATES PATENT AND TRADEMARK OFFICE
CERTIFICATE OF CORRECTION

PATENT NO. : 5,962,768
DATED : October 5, 1999
INVENTOR(S) : Cornelissen et al.

It is certified that error appears in the above-identified patent and that said Letters Patent is hereby corrected as shown below:

Column 7:

Line 6, change "C58C1-Rif®" to --C58C1-Rif$^R$--.
Line 16, change "C58C1-Rif®" to --C58C1-RIf$^R$--.
Line 17, change "C58C1-Rif®" to --C58C1-RIf$^R$--.
Line 19, change "C58C1-Rif®" to --C58C1-RIf$^R$--.
Line 25, change "C58C1-Rif®" to --C58C1-RIf$^R$--.
Line 26, change "C58C1-Rif®" to --C58C1-RIf$^R$--.
Line 41, change "C58C1-Rif®" to --C58C1-RIf$^R$--.
Line 42, change "C58C1-Rif®" to --C58C1-RIf$^R$--.
Line 48, change "C58C1-Rif®" to --C58C1-RIf$^R$--.
Line 51, change "C58C1-Rif®" to --C58C1-RIf$^R$--.

Signed and Sealed this

Nineteenth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 5,962,768
DATED : October 5, 1999
INVENTOR(S) : Cornelissen et al.

It is certified that error appears in the above-identified patent and that said Letters Patent is hereby corrected as shown below:

Title page,
Please insert, as follow:
-- item [73] Assignee: Plant Genetic Systems N.V., Brussels, Belgium --

Title page,
Line 19, under "Other Publications", please change "Van Vhieu et al." to -- Van Nhieu et al.

Column 6,
Line 53, change "nPtll" to -- nptll --.

Column 7,
Line 6, change "C58C1 –Rif®" to -- C58C1-Rif$^R$ --.
Line 16, change "C58C1 –Rif®" to -- C58C1-Rif$^R$ --.
Line 17, change "C58C1 –Rif®" to -- C58C1-Rif$^R$ --.
Line 19, change "C58C1 –Rif®" to -- C58C1-Rif$^R$ --.
Line 25, change "C58C1 –Rif®" to -- C58C1-Rif$^R$ --.
Line 26, change "C58C1 –Rif®" to -- C58C1-Rif$^R$ --.
Line 41, change "C58C1 –Rif®" to -- C58C1-Rif$^R$ --.
Line 42, change "C58C1 –Rif®" to -- C58C1-Rif$^R$ --.
Line 48, change "C58C1 –Rif®" to -- C58C1-Rif$^R$ --.
Line 51, change "C58C1 –Rif®" to -- C58C1-Rif$^R$ --.

This certificate supercedes Certificate of Correction issued June 19, 2001.

Signed and Sealed this

Sixteenth Day of October, 2001

*Attest:*

NICHOLAS P. GODICI
*Attesting Officer*    *Acting Director of the United States Patent and Trademark Office*